(12) United States Patent
Okura

(10) Patent No.: US 9,856,523 B2
(45) Date of Patent: Jan. 2, 2018

(54) METHOD FOR HIGH ACCURACY GENOMIC ANALYSIS UTILIZING HYBRIDIZATION AND ENHANCED DISSOCIATION

(76) Inventor: Michael Okura, Honolulu, HI (US)

( * ) Notice: Subject to any disclaimer, the term of this patent is extended or adjusted under 35 U.S.C. 154(b) by 71 days.

(21) Appl. No.: 13/445,873

(22) Filed: Apr. 12, 2012

(65) Prior Publication Data

US 2012/0289421 A1    Nov. 15, 2012

Related U.S. Application Data

(60) Provisional application No. 61/474,727, filed on Apr. 12, 2011.

(51) Int. Cl.
*C40B 30/04* (2006.01)
*C12Q 1/68* (2006.01)
*C40B 60/12* (2006.01)

(52) U.S. Cl.
CPC ......... *C12Q 1/6837* (2013.01); *C12Q 1/6874* (2013.01); *C12Q 2527/107* (2013.01)

(58) Field of Classification Search
CPC .......... G01N 1/38; G01N 21/00; G01N 21/17; G01N 21/62; G01N 21/63; G01N 21/64;
(Continued)

(56) References Cited

U.S. PATENT DOCUMENTS 6,150,103 A    11/2000 Ness et al.
7,166,451 B1    1/2007 Yang et al.
(Continued)

FOREIGN PATENT DOCUMENTS

EP           1 046 717 A2    4/2000
WO    WO 2008124847 A2 * 10/2008 ............. G06F 19/22
(Continued)

OTHER PUBLICATIONS

Carré, Alain et al., 2007, Silanes and Other Coupling Agents, Ed. K.L. Mittal, vol. 4, pp. 1-14.*
(Continued)

*Primary Examiner* — Amy M Bunker
(74) *Attorney, Agent, or Firm* — Intellectual Property Law Group LLP

(57) ABSTRACT

Methods and an apparatus according to the present invention, can be used in capture/enrichment, gene expression profiling and targeted sequencing. Provided are methods for improving accuracy and stringency of microarrays and/or other genomic analysis methods relying on nucleic acid hybridization and melting curve analysis by controlling surface chemistry. This method comprises producing a positively charged surface or surface coating, on the surface of microarray slides or other types of surfaces similarly purposed, such as micro beads, which enhances melting curve analysis to the point of allowing detection or differentiation of small changes in sequences between nucleic acid binding partners. Also provided is an improved microarray reader machine, to collect melting curve data on microarray slides. The accuracy or resolution of melting curve analysis was to be sufficient to distinguish between the melting of perfect matched dsDNA and dsDNA with the smallest possible change in sequence, a one base pair mismatch.

18 Claims, 8 Drawing Sheets

(58) Field of Classification Search
CPC .... G01N 21/6428; G01N 25/00; G01N 25/20; G01N 33/00; G01N 33/483; G01N 33/487; G01N 33/48707; G01N 33/48721; G01N 33/58; G01N 33/582; G01K 17/00; C40B 30/04
USPC .......................................................... 506/9
See application file for complete search history.

(56) References Cited

U.S. PATENT DOCUMENTS

| | | | |
|---|---|---|---|
| 2002/0090614 A1 | 7/2002 | Zhang et al. | |
| 2004/0091862 A1 | 5/2004 | Brandenburg et al. | |
| 2005/0042638 A1 | 2/2005 | Arnold et al. | |
| 2007/0003958 A1 | 1/2007 | Okamoto et al. | |
| 2007/0128628 A1* | 6/2007 | Krupp et al. | 435/6 |
| 2007/0178516 A1* | 8/2007 | Sosnowski et al. | 435/6 |
| 2009/0182120 A1 | 7/2009 | Utermohlen et al. | |
| 2010/0105033 A1* | 4/2010 | Sun et al. | 435/6 |
| 2010/0204461 A1* | 8/2010 | Beadling et al. | 536/24.3 |

FOREIGN PATENT DOCUMENTS

| | | | |
|---|---|---|---|
| WO | WO 2010/038170 A1 | 9/2009 | |
| WO | WO 2009/158451 A1 | 12/2009 | |
| WO | WO 2009158451 A1 * | 12/2009 | ............. B01L 7/00 |

OTHER PUBLICATIONS

Xie, Hong et al., 2004 Clinical Chemistry 50: 1231-1233.*
Chiu, Sung-Kay et al., 2003 Biochem J 374: 625-632.*
Tan et al., Synthesis of Positively Charged Siliver Nanoparticles Via Photoreduction of AnNO3 in Branched Polyethyleneimini/HEPES Solutions, Langmuir, 2007, 23, 9836-9843.*
Sperling et al., Surface Modification, Functionalization and Bioconjugation of Colloidal Inorganic Nanoparticles, Phil. Trans. R. Soc. A, 2010, 368, 1333-1383.*
Lazar, M., Electric Charges, Let's Review, Physics—The Physical Setting, Third Edition, 2004, 176-178.*
Schott, Nexterion Slide E, Epoxysilane Coating, 2009, 1-3.*
China Search Report dated Nov. 20, 2014 for corresponding Chinese Application No. 2012800287320.
Supplementary European Search Report dated Oct. 31, 2014 for corresponding European Application No. 12771263.6.
International Search Report, dated Jul. 27, 2012, for corresponding International Application No. PCT/US2012/33406.
Written Opinion of the International Searching Authority, dated Jul. 27, 2012, for corresponding International Application No. PCT/US2012/33406.
Vainrub et al., Surface electrostatic effects in oligonucleotide microarrays: control and optimization of binding. Biopolymers, Feb. 2003, vol. 68, No. 2, pp. 265-270.
Van Ness et al., A versatile solid support system for oligodeoxynucleotide probe-based hybridization assays. Nucleic Acids Res., Jun. 25, 1991 (Jun. 25, 1991), vol. 19, No. 12, pp. 3345-3350.
Spink et al., Thermodynamics of the Binding of a Cationic Lipid to DNA, J. Am. Chem. Soc., vol. 119, pp. 10920-10928 (1997).
Ogino, et al., Sensitive Sequencing Method for KRAS Mutation Detection by Pyrosequencing, J. Molecular Diagnostics, Aug. 2005, 7(3): 413-421; Abstract, p. 416, Fig 4.
Simi et al., High-Resolution Melting Analysis for Rapid Detection of KRAS, BRAF, and PIK3CA Gene Mutations in Colorectal Cancer, Am. J. Clin. Pathol., vol. 130, pp. 247-253 (2008).
Bai, et al., Nanoparticles Affect PCR Primarily via Surface Interactions with PCR Components: Using Amino-Modified Silica-Coated Magnetic Nanoparticles as a Main Model, ACS Applied Materials & Interfaces, Jun. 24, 2015, 7(24):12142-53; Abstract.
International Search Report, dated Apr. 4, 2017, for International Application No. PCT/US2016/066227.
Written Opinion of the International Searching Authority, dated Apr. 4, 2017, for International Application No. PCT/US2016/066227.

* cited by examiner

METHOD FOR HIGH ACCURACY GENOMIC ANALYSIS UTILIZING HYBRIDIZATION AND ENHANCED DISSOCIATION

CROSS-REFERENCE TO RELATED APPLICATIONS

The present application claims priority to U.S. provisional patent application Ser. No. 61/474,727 filed on Apr. 12, 2011, which is herein incorporated by reference in its entirety.

FIELD OF INVENTION

The present invention generally relates to microarray technology, and more particularly to methods and an apparatus for improving the accuracy of microarray gene expression profiling and single nucleotide polymorphism (SNP) analysis.

Microarray technology has been the dominant genomics methodology but suffered from problems with repeatability and inaccuracy. In the quest for superior methods for genomics analysis, an abundance of next generation sequencing (NGS) methods were developed since the late 2000s. This allowed sequencing the human genome to drop in price from about $3 billion (2004) to approximately $20 k per genome as of early 2010. Genomics is certainly one of the fastest developing areas of the life sciences but large gaps continue to exist in the price performance of NGS in relation to other genomics techniques. While there have been dramatic pricing drops for the actual sequencing process, the price of NGS when used for gene expression profiling and SNP analysis is not competitive with microarrays that range in the hundreds of dollars per assay.

Furthermore, NGS techniques were developed for whole genome sequencing and sequence all DNA present in the sample. Analysis of specific parts of the genome or a subset of genes requires capture-enrichment assays. These consist of standard microarray chips which hybridize specific sequences but allow other unwanted sequences to be washed away. While, enrichment can be over 100 fold using this methodology, only between 30% to 60% of the captured DNA can come from the desired sections of the genome. As a result, capture enrichment assays typically are not very efficient and the depth or redundancy of sequence coverage varies with each experiment.

The Real-Time Array originated as a method for improving the accuracy of microarray gene expression profiling. The use of its technology is envisioned to simplify and lower cost for single nucleotide polymorphism (SNP) analysis. Melting curve analysis of double stranded DNA (dsDNA) has been practiced since the early 1960s in single tube reactions also referred to as liquid phase reactions. These experiments were done in tubes or liquid phase with the DNA free in solution. Since the discovery of melting analysis, the bulk of research has been spent studying liquid phase reactions. A common limitation to liquid phase melting curves is the inability to achieve one base pair resolution of detection. However, the application of melting curve analysis to the microarray or solid phase reaction is a relatively new and not completely understood process.

At the present time, there exists a need for a method and apparatus that can utilize measurement of the melting of target DNA away from probes bound to a glass microarray and that should distinguish between perfect match and mismatches on an individual probe spot and approximate the relative amounts of each species at a very low cost. Further, it would be advantageous to have a method that can simultaneously analyze DNA sequence data while functioning as capture-enrichment tool, has sensitivity, is not time-consuming and is efficient safe and effective. Moreover, this method and apparatus can be useful in health care, environmental research, pharmaceutical industry and food industry and are applicable for many other diagnostic, biotechnical and scientific purposes.

SUMMARY

The present invention is directed to methods and an apparatus for high accuracy genomic analysis platform utilizing hybridization and chemically enhanced dissociation that meets these needs. The methods and apparatus according to the present invention, can be used in capture/enrichment, gene expression profiling and targeted sequencing.

Embodiments of the present invention provide a solution to improving the accuracy and stringency of microarrays and/or other genomic analysis methods relying on nucleic acid hybridization and melting curve analysis. Methods are provided by controlling the surface chemistry of the slide and development of an improved microarray reader. In an advantageous embodiment, there is a method of producing, through initial synthesis, manufacture or through secondary applications, a positively charged surface or surface coating, on the surface of microarray slides or other types of surfaces used for similar purposes, such as micro beads, which enhances melting curve analysis to the point of allowing the detection or differentiation of small changes in sequences between nucleic acid binding partners. As example embodiments, polyethyleneimine, epoxide or a variety of other positively charged chemicals or even the use of an electrical current across the surface to generate a positive charge, can be used for the enhancement of DNA microarray melting curve analysis or other hybridization based assays.

The present invention is directed to a method of capture/enrichment, detecting the presence, measuring the amount or verifying the sequence of a target polynucleotide of interest in a test sample. The method comprises the steps of forming a reaction mixture by combining in an assay medium: (i) a first reagent comprising a first probe bound to a solid particle, and (ii) an aliquot of the test sample suspected of containing the target nucleotide sequence. The first probe comprises a first single stranded nucleic acid fragment complementary to a first of two separated strands of a selected segment of the target nucleotide sequence. The solid particle is a positively charged solid particle. The first probe is complementary to mutually exclusive portions of the target polynucleotide sequence;

The reaction mixture is then subjected under denaturing conditions rendering the target polynucleotide sequence in the sample to be single stranded. The reaction mixture is then incubated under hybridization conditions to cause hybridization between the first probe and the first strand of the selected segment of the target polynucleotide sequence. In the presence of the target polynucleotide, substantially all of the first probe will be hybridized to the first strand of the selected segment of the target polynucleotide sequence producing bound target polynucleotide sequence. The reaction mixture to disassociation conditions.

The reaction mixture is then monitored. Preferably, disassociation correlates with changes in the presence of the bound target polynucleotide providing disassociation curve analysis.

The positively charged solid particle enhances thermal disassociation characteristics for analysis, to the point of allowing the detection, amount or differentiation of small sequence differences between nucleic acid hybrids in the target polynucleotide and the first probe. The small sequence differences can be down to one base pair.

The target polynucleotide can be a segment of DNA or RNA. The first probe can be a DNA or RNA fragment. Typically, the first probe can be bound to the solid particle by a linker. Preferably, the solid particle can be selected from the group consisting of polystyrene, microbeads, glass, metal, charcoal, colloidal gold, bentonite, polypropylene, plastics and silica. More preferably, the solid particle is glass. Even more preferably, the solid particle is a glass slide and is a micro array glass slide. The micro array glass slide comprises from about 10 to about 4.2 million probes.

The positively charged particle comprises a surface coating of positively charged chemicals. Preferably, the positively charged chemicals can be selected from the group consisting of polyethyleneimine, epoxide, amine and any chemical compound with a positive charge. More preferably, the positively charged chemical is polyethyleneimine and is present in the amount from about 1% to about 10%.

The positively charged particle can comprise a surface coating of positively charged chemicals generated by use of an electrical current across the surface to generate a positive charge.

Typically, the target polynucleotide sequence can include a label. The label can be a fluorescent dye selected from the group consisting of 2-((iodoacetyl)amino)ethyl)aminonapthylene-1-sulfonic acid) (1,5-IEDANS), fluorescein, Bodipy, FTC, Texas Red, phycoerythrin, rhodamines, carboxytetramethylrhodamine, DAPI, indopyras dyes, Cascade Blue, Oregon Green, eosins, erythrosin, pyridyloxazoles, benzoxadiazoles, aminonapthalenes, pyrenes, maleimides, coumarins, Lucifer Yellow, Propidium iodide, porhyrins, CY3, CY5, CY9, lanthanides, cryptates, and lanthanide chelates.

Preferably, the step of exposing the reaction mixture to disassociation conditions can be carried out over a temperature range from about 0° C. to about 100° C., with temperature increase increments of from about 0.01° C. to about 5.0° C.

The steps of forming, subjecting, incubating, exposing and monitoring were carried out by an automated micro array device.

The first probe can include a label. The label can be a fluorescent dye selected from the group consisting of 2-((iodoacetyl)amino)ethyl)aminonapthylene-1-sulfonic acid) (1,5-IEDANS), fluorescein, Bodipy, FTC, Texas Red, phycoerythrin, rhodamines, carboxytetramethylrhodamine, DAPI, indopyras dyes, Cascade Blue, Oregon Green, eosins, erythrosin, pyridyloxazoles, benzoxadiazoles, aminonapthalenes, pyrenes, maleimides, coumarins, Lucifer Yellow, Propidium iodide, porhyrins, CY3, CY5, CY9, lanthanides, cryptates, and lanthanide chelates.

The reaction mixture can further include a buffer.

The present invention is directed to a micro array apparatus for genome sequence analysis comprising: a base structure comprises: a real-time micro array reader cassette; wherein the cassette configured to hold microarray slides; a thermal control chamber comprising a heat control unit and a fluids control unit; wherein the heat control unit measures temperature data for melting curve analysis; an optical system for measuring the presence or absence, and concentration of labeled nucleic acid sample providing the concentration data for melting curve analysis; and an automatic focusing system. Preferably, a computerized Z-axis is added to the thermal control chamber to speed up a focusing procedure and allow automatic incremental adjustments of focus. Preferably, the melting curve data is sufficient to distinguish between the melting of different sequences of target DNA with one base pair sensitivity for each probe spot of a microarray, allowing for scanning of entire genome sequencing.

In summary, The Real-Time Genomics array of the present invention is a next generation microarray technology that improves the accuracy of the microarray system and fills in the gaps not covered by NGS.

BRIEF DESCRIPTION OF DRAWINGS

These and other features, aspects, and advantages of the present invention will become better understood with reference to the following description, appended claims, and accompanying drawings where:

DETAILED DESCRIPTION

According to the present invention, there is provided a method for improving the accuracy and stringency of microarrays and/or other genomic analysis methods relying on nucleic acid hybridization and melting curve analysis by controlling the surface chemistry of the slide. The method comprises producing a positively charged surface or surface coating, on the surface of microarray slides or other types of surfaces used for similar purposes, such as micro beads, which enhances melting curve analysis to the point of allowing the detection or differentiation of small changes in sequences between nucleic acid binding partners. There is also provided an improved microarray reader machine, to collect melting curve data on microarray slides containing 1000 probe spots or more. In addition, the accuracy or resolution of melting curve analysis was to be sufficient to distinguish between the melting of perfect matched dsDNA and dsDNA with the smallest possible change in sequence, a one base pair mismatch.

In preferred embodiments of the present invention, the methods and apparatus according to the present invention, can be used in capture/enrichment, gene expression profiling and targeted sequencing. Particularly, in an embodiment of the present invention, there is a method of capture/enrichment of a target polynucleotide of interest in a test sample. In another embodiment of the present invention, there is a method of detecting the presence of a target polynucleotide of interest in a test sample. In yet another embodiment of the invention, there is a method of measuring the amount of a target polynucleotide of interest in a test sample. In another and more preferable embodiment of the present invention there is a method of verifying the sequence of a target polynucleotide of interest in a test sample.

Figures 1A, 1B, 1C:
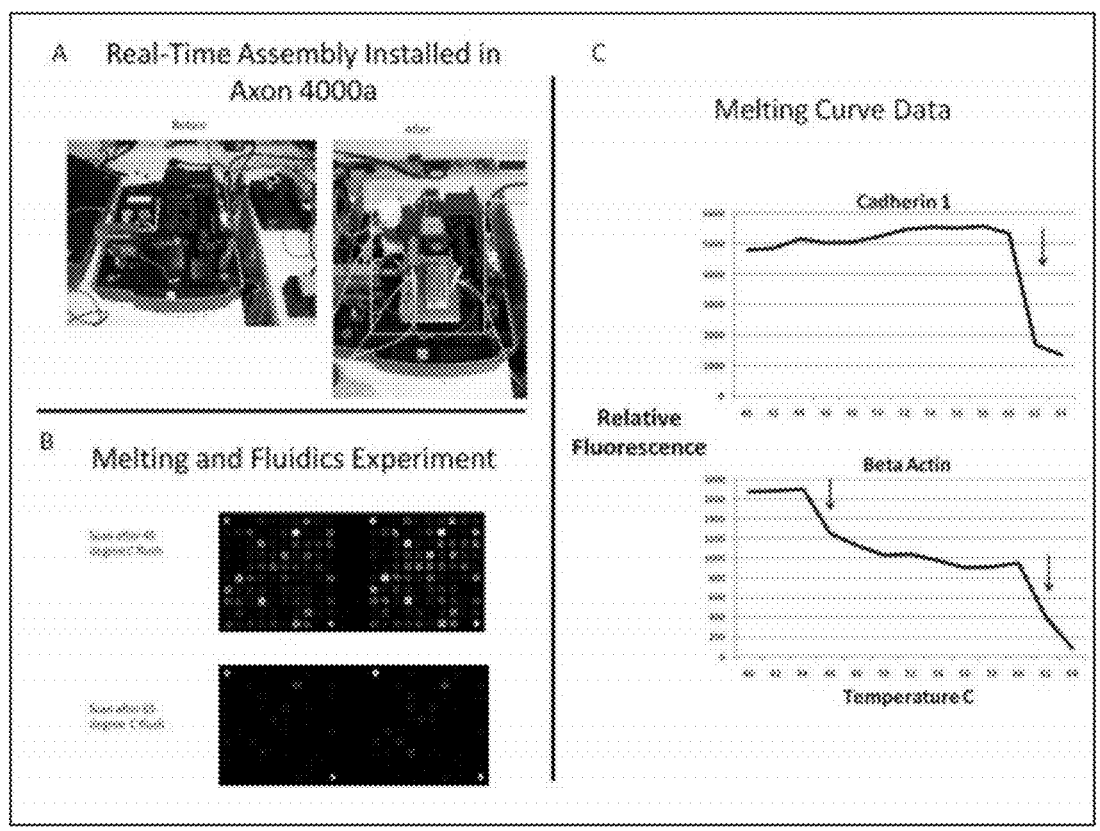
FIG. 1A illustrates an exemplary prototype Real-Time Array reader machine according to an embodiment of the present invention.
FIG. 1B illustrates an exemplary comparison of microarray images obtained during a melting experiment between the temperatures of 45° and 65° C. according to the embodiments of the present invention.
FIG. 1C illustrates exemplary results of array hybridized with human cDNA stained with Cy3 dye according to the embodiments of the present invention.

In one particular embodiment of the present invention, preliminary data obtained suggests that creating melting curve analysis on a microarray significantly improves the accuracy of microarrays. According to the present invention, FIG. 1A illustrates an exemplary device according to the present invention. With respect to FIG. 1A, a cost saving measure the first Real-Time Array reader was a modified Axon 4000a (Molecular Devises, Sunnyvale, Calif.) machine in which heat control and fluidics were combined with existing scanning capability. Initial experiments utilized a commercial microarray chip "Check It Chips" with large 300 µM probe spots and 70 mer probe sequences for the human genome printed in blocks of 100 spots for a total of 2 blocks or 200 probe spots per array (commercially available from Arrayit Corporation, Sunnyvale, Calif.). According to the present invention, these slides typically have an amine coated surface and probes attached via UV cross linking. Human cDNA stained with Cy3 dye (Arrayit Corp.) was used as target DNA for hybridization. Typically, melting experiments can be carried out in a temperature range from about 0° C. to about 100° C. Preferably, melting experiments were carried out over a temperature range from about 40° C. to about 70° C., preferably with temperature increase increments of 1° C. and fluidics buffer flush of 600 µl of 2.5×SSC.

Embodiments of the present invention provide a solution to improving the accuracy and stringency of microarrays and/or other genomic analysis methods relying on nucleic acid hybridization and melting curve analysis. Methods are provided by controlling the surface chemistry of, for example, a micro array slide and development of an improved microarray reader. In an advantageous embodiment, there is a method of producing, through initial synthesis, manufacture or through secondary applications, a positively charged surface or surface coating, on the surface of microarray slides or other types of surfaces used for similar purposes, such as micro beads, which enhances melting curve analysis to the point of allowing the detection or differentiation of small changes in sequences between nucleic acid binding partners. As example embodiments, polyethyleneimine, epoxide or a variety of other positively charged chemicals or even the use of an electrical current across the surface to generate a positive charge, can be used for the enhancement of DNA microarray melting curve analysis or other hybridization based assays.

The present invention is directed to a method of capture/enrichment, detecting the presence, measuring the amount or verifying the sequence of a target polynucleotide of interest in a test sample. The method comprises the steps of forming a reaction mixture by combining in an assay medium: (i) a first reagent comprising a first probe bound to a solid particle, and (ii) an aliquot of the test sample suspected of containing the target nucleotide sequence. The first probe comprises a first single stranded nucleic acid fragment complementary to a first of two separated strands of a selected segment of the target nucleotide sequence. The solid particle is a positively charged solid particle. The first probe is complementary to mutually exclusive portions of the target polynucleotide sequence;

The reaction mixture is then subjected under denaturing conditions rendering the target polynucleotide sequence in the sample to be single stranded. The reaction mixture is then incubated under hybridization conditions to cause hybridization between the first probe and the first strand of the selected segment of the target polynucleotide sequence. In the presence of the target polynucleotide, substantially all of the first probe will be hybridized to the first strand of the selected segment of the target polynucleotide sequence producing bound target polynucleotide sequence. The reaction mixture to disassociation conditions.

The use of nucleic acid hybridization as an analytical tool is based on the double stranded duplex structure of DNA. The hydrogen bonds between the purine and pyrimidine bases of the respective strands in double stranded DNA can be reversibly broken. The two complementary strands of DNA resulting from this melting or denaturation of DNA will associate (also referred to as reannealing or hybridization) to reform the duplexed structure. Contact of a first single stranded nucleic acid, either DNA or RNA, which comprises a base sequence sufficiently complementary to a second stranded nucleic acid under appropriate conditions, will result in the formation of nucleic acid hybrids, as the case may be.

The reaction mixture is then monitored. Preferably, dissociation correlates with changes in the presence of the bound target polynucleotide providing disassociation curve analysis. The positively charged solid particle enhances thermal disassociation characteristics for analysis, to the point of allowing the detection, amount or differentiation of small sequence differences between nucleic acid hybrids in the target polynucleotide and the first probe. The small sequence differences can be down to one base pair.

Preferably, the target polynucleotide can be a segment of deoxyribonucleic acid (DNA) sequence or ribonucleic acid (RNA) sequence. The target polynucleotide sequence of interest can be any polynucleotide sequence present naturally in a sample. It can be in a material in or derived from a cellular system. The polynucleotide sequence can be any gene or polynucleotide sequence of interest (DNA or RNA).

In a preferred embodiment of the present invention, the first probe can be a nucleic acid fragment, preferably, a DNA or RNA fragment. More preferably, the first probe comprises a first single stranded nucleic acid fragment complementary to a first of two separated strands of a selected segment of the target polynucleotide sequence. The nucleic acid fragments can be produced or obtained by any method known to those of ordinary skill in the art, e.g., synthetic production methods or enzymatic production methods, both in vitro and in vivo. DNA and RNA probes preferably are single stranded nucleic acid molecules generally synthesized by gene machines or made using recombinant DNA methods known to those skilled in the art.

Preferably, the first probe will exhibit detectable hybridization at one or more points with the target polynucleotide sequence of interest. More preferably, the nucleic acid probe fragment attached to the solid particle can be of almost any length, provided that the fragment is long enough to form a stable nucleic acid hybrid with the selected segment of the target polynucleotide sequence. The first probe nucleic acid fragment will typically have a minimum 4-base sequence, one case greater than an amino acid codon. Preferably, the first probe nucleic acid fragment is from about 4 to about 20 nucleotides in length. The more nucleotides, the greater the specificity.

Typically, the first probe can be bound to the solid particle by a spacer linker.

Preferably, the solid particle can be any insoluble particle that is capable of attaching DNA or RNA. The DNA or RNA can be attached to the solid particle by any known methods known to those of ordinary skill of the art including but not limited to chemical bonds, including covalent bonds, ionic bonds and electrostatic attractions. Preferably, the solid particle can be selected from the group consisting of polystyrene, microbeads, glass, metal, charcoal, colloidal gold, bentonite, polypropylene, plastics and silica. More preferably, the solid particle is glass. Even more preferably, the solid particle is a glass slide and is a micro array glass slide.

In a more preferred embodiment of the present invention, any number of probes can be possible and can be tailored accordingly. For example, for simple applications, as little as 10 probe spots can be used, for example, on a micro array slide and for a high throughput, millions of probe spots can be used and tailored accordingly. Determining the number of probes to be used can be accomplished by any method known to those skilled in the art. Preferably, the micro array glass slide comprises from about 10 to about 4.2 million probes.

According to the present invention, probes comprise a single stranded nucleic acid fragment complementary to a first of two separated strands of a selected segment of a target polynucleotide sequence. The nucleic acid fragments can be fragments from deoxyribonucleic acid (DNA) or ribonucleic acid (RNA) sequences. Preferably the nucleic acid fragment is single stranded. The nucleic acid fragments can be produced or obtained by any method known to those of ordinary skill in the art, e.g., synthetic production methods or enzymatic production methods, both in vitro and in vivo. DNA and RNA probes are single-stranded nucleic acid molecules generally synthesized by so called gene machines or made using recombinant DNA methods.

In yet another preferred embodiment of the present invention, the first probe strands are not attached directly to the solid particle, such as a microarray surface, but preferably attached by using a linker, which can elevate the DNA off the surface. More preferably, the linkers can be made primarily to allow the DNA to be at a greater distance off the surface of the slide, but can also have additional chemical properties, for example, if the linker were to have a positive charge, it may be able to replicate the results achieved with just a positively charged surface.

As used herein, the term "hybridization conditions" means those conditions which enable the hybridization between the first probe attached to the solid particle to a first strand of the selected segment of target polynucleotide sequence. According to the present invention, hybridization techniques and melting curve analysis are typically known to those skilled of ordinary skill in the art and can be used in the present invention.

The choice of solid particle can be governed by the effect of rate of hybridization and binding of the probe to the target DNA. The solid particle preferably should provide sufficient sensitivity in order to detect the amount of target nucleotide sequence available for hybridization. Other consideration will be the ease of synthesis of the probe, the availability of instrumentation, the ability to automate and convenience.

In yet a preferred embodiment of the present invention, by controlling the surface chemistry of the solid particle. More preferably, the solid particle will have a positively charged surface or surface coating, which enhances melting curve analysis to the point of allowing the detection or differentiation of small changes in sequences between nucleic acid binding partners, the detection or differentiation of small changes in sequences can be up to one base pair.

In yet another preferred embodiment of the present invention, any cationic or other positively charged chemicals can be used to coat the solid particle surface. More preferably, the positively charged particle comprises a surface coating of positively charged chemicals. Preferably, the positively charged chemicals can be selected from the group consisting of polyethyleneimine, epoxide, amine and including but not limiting any chemical compound known to those with ordinary skill in the art with a positive charge. More preferably, the positively charged chemical is polyethyleneimine and is present in the amount from about 1% to about 10%.

In yet an alternate preferred embodiment of the present invention, the positively charged particle can comprise a surface coating of positively charged chemicals generated by use of an electrical current across the surface to generate a positive charge that can be used for the enhancement of DNA micro array melting curve analysis or other hybridization based assays.

Typically, the target polynucleotide sequence can include a label. The label can be any label or tag known to those skilled in the art. The label can include dyes, radioactive labels, gold, silver, beads, antibody or any other label known to those skilled in the art to label or tag a polynucleotide sequence. Preferably, the label can be a fluorescent dye selected from the group consisting of 2-((iodoacetyl)amino)

ethyl)aminonapthylene-1-sulfonic acid) (1,5-IEDANS), fluorescein, Bodipy, FTC, Texas Red, phycoerythrin, rhodamines, carboxytetramethylrhodamine, DAPI, indopyras dyes, Cascade Blue, Oregon Green, eosins, erythrosin, pyridyloxazoles, benzoxadiazoles, aminonapthalenes, pyrenes, maleimides, coumarins, Lucifer Yellow, Propidium iodide, porhyrins, CY3, CY5, CY9, lanthanides, cryptates, and lanthanide chelates. More preferably, CY3 is used as the dye.

In a more preferred embodiment of the present invention, the step of exposing the reaction mixture to disassociation conditions, means exposing the reaction mixture to any melting temperature or melting conditions known to those skilled in the art. Disassociation and melting can be used interchangeably from here throughout the specification. Disassociation or melting conditions can be any conditions known but not limited to those with skilled in the art, including heat, chemicals, electrical current or other types of fluid or sound waves. More preferably, disassociation means melting conditions.

In the disassociation conditions, the melting temperature can be calculated using the probe sequence and buffer composition. The melting temperature typically is the lowest temperature that will allow all of the target to be release from the probe. If the melting temperature is too low the target will not be released. On the other hand using a high melting temperature can have no negative effect on the results other than consuming more time and energy to finish the experiment.

Preferably, when the determining the range of temperature for the real-time melting (dissociation) reaction to take place it usually starts at or below the hybridization temperature and ends a little above the melting temperature.

Typically, the step of exposing the reaction mixture to disassociation conditions can be carried out over a temperature range from about 0° C. to about 100° C. Preferably, the step of exposing the reaction mixture to disassociation conditions can be carried out over a temperature range from about 40° C. to about 70° C., with temperature increase increments of from about 0.01° C. to about 5.0° C. Preferably, the temperature increase increments can be carried out from about 0.01° C. to about 5.0° C.

According to a preferred embodiment of the present invention, in the step of exposing the reaction mixture to melting conditions, the temperature range can vary depending on the probe sequence and probe length, and can be adjusted according to those skilled in the art. Typically, in the step of exposing the reaction to melting conditions, the experiment can be carried out over a temperature range from about 0° C. to about 100° C. Preferably, in the step of exposing the reaction to melting conditions, the experiment can be carried out over a temperature range from about 40° C. to about 70° C.

Typically, the range of temperature over which the experiment can be conducted is determined by the hybridization temperature and the melting temperature of the target sequence and probes. Before the melting reaction is conducted, hybridization can be performed and is accomplished at one specific temperature. Typically, the hybridization temperature can be a temperature suggested by the manufacturing company, for example, of the micro array and a common hybridization temperature typically can be 45° C. Preferably, the range of temperature can be determined by calculating or estimating the temperature in which the target polynucleotide sequence is most likely to bind its complementary first probe. This estimated temperature can vary according to the sequence of nucleic acids and type of buffer used during hybridization. It is well known to those with ordinary skill in the art, that the higher the GC content and the longer the sequence, the higher the hybridization temperature. Using a hybridization temperature lower than one calculated for the best specific hybridization can allow more non-specific binding to occur between probe and target. Using a hybridization temperature that is too high may not allow target to bind probes.

In yet another embodiment of the present invention, in the step of exposing the reaction mixture to disassociation or melting conditions, the temperature increase increments can be from about 0.01° C. to about 5.0° C. Preferably, the temperature increase increments can be from about 0.01° C. to about 3.0° C. The temperature increase increment can be varied according to those skilled in the art, to how much resolution is needed in the melting curve graph analysis. For example, typically, for the following experiments conducted, a 1° C. temperature increase worked well, however, a temperature increment increase of less than 1° C. could add more data points to the graph generated for analysis, thereby increasing the resolution of the melting curve however, would have consumed more time. Accordingly, using a temperature increase increment of more than 1° C. can speed up the experiment, however, there would be a decrease in the resolution of the melting curve. If the resolution of the melting curve was too low, determining the exact temperature in which target and probe melted apart (Tm) would not be possible. Preferably, the temperature increase increment is about 1° C.

The steps of forming, subjecting, incubating, exposing and monitoring preferably are carried out by an automated micro array device.

The first probe can include a label. The label can be any label or tag known to those skilled in the art. The label can include dyes, radioactive labels, gold, silver, beads, antibody or any other label known to those skilled in the art to label or tag a polynucleotide sequence. Preferably, the label can be a fluorescent dye selected from the group consisting of 2-((iodoacetyl)amino)ethyl)aminonapthylene-1-sulfonic acid) (1,5-IEDANS), fluorescein, Bodipy, FTC, Texas Red, phycoerythrin, rhodamines, carboxytetramethylrhodamine, DAPI, indopyras dyes, Cascade Blue, Oregon Green, eosins, erythrosin, pyridyloxazoles, benzoxadiazoles, aminonapthalenes, pyrenes, maleimides, coumarins, Lucifer Yellow, Propidium iodide, porhyrins, CY3, CY5, CY9, lanthanides, cryptates, and lanthanide chelates.

More preferably, CY3 is used as the dye. The fluorescent polynucleotide probes are especially useful in automatic or semiautomatic recording of the results combined with continuous flow systems and instruments.

Preferably, the reaction mixture can further include a buffer. Any buffer known to those of ordinary skill in the art can be used. More preferably, the buffer is selected based on the buffer ionic strength, which can affect the reaction.

The present invention is directed to a micro array apparatus for genome sequence analysis comprising: a base structure comprises: a real-time micro array reader cassette; wherein the cassette configured to hold microarray slides; a thermal control chamber comprising a heat control unit and a fluids control unit; wherein the heat control unit measures temperature data for melting curve analysis; an optical system for measuring the presence or absence, and concentration of labeled nucleic acid sample providing the concentration data for melting curve analysis; and an automatic focusing system. Preferably, a computerized Z-axis is added to the thermal control chamber to speed up a focusing procedure and allow automatic incremental adjustments of focus. Preferably, the melting curve data is sufficient to distinguish between the melting of different sequences of target DNA with one base pair sensitivity for each probe spot of a microarray, allowing for scanning of entire genome sequencing. The optical system preferably provides fluorescence intensity data, whereas the heat control unit typically provides the reaction mixture temperature data.

In an embodiment of the present invention, FIG. 1B illustrates comparison of microarray images obtained during a melting experiment between the temperatures of 45° and 65° C. As FIG. 1B depicts, repeated cycles of temperature increase, buffer flush, and scans melted away most of the bound target DNA on the slide away by 65° C. confirming release of target DNA.

According to a preferred embodiment of the present invention, in the step of exposing the reaction mixture to melting conditions, the temperature range can vary depending on the probe sequence and probe length, and can be adjusted according to those skilled in the art. Typically, in the step of exposing the reaction to melting conditions, the experiment can be carried out over a temperature range from about 0° C. to about 100° C., preferably from about 40° C. to about 70° C.

In yet another embodiment of the present invention, in the step of exposing the reaction mixture to melting conditions, the temperature increase increments can be from about 0.01° C. to about 5.0° C. Preferably, the temperature increase increments can be from about 0.01° C. to about 3.0° C. The temperature increase increment can be varied according to those skilled in the art, to how much resolution is needed in the melting curve graph analysis. For example, typically, for the following experiments conducted, a 1° C. temperature increase worked well, however, a temperature increment increase of less than 1° C. could add more data points to the graph generated for analysis, thereby increasing the resolution of the melting curve however, would have consumed more time. Accordingly, using a temperature increase increment of more than 1° C. can speed up the experiment, however, there would be a decrease in the resolution of the melting curve. If the resolution of the melting curve is too low, determining the exact temperature in which target and probe melted apart (Tm) would not be possible. Preferably, the temperature increase increment is about 1° C.

In yet another embodiment of the present invention, FIG. 1C depicts results of array hybridized with human cDNA stained with Cy3 dye. Melting analysis was performed over the temperature range of 40°-64° C. with readings at 2° C. intervals. Graph A (Cadherin 1 probe) depicts a melting curve showing one large melting point (arrow) at about 63° C. indicating the presence of one major hybridization product. However, Graph B (Beta Actin probe) depicts at least two major melting points (arrows) at 46° and 62° C. This result indicates the presence of multiple hybridization products. Conventional microarray analysis is not capable of making this distinction. The relative abundance of each hybridization product can be inferred from the graph. FIG. 1C shows when actual melting curves were plotted by compiling the fluorescence intensity data at each temperature of scanning for each probe spot, well-formed curves were obtained. Remarkably, these curves exhibited a sharp slope or drop at which DNA melted away from the array which allowed easy discernment of the temperature of melting (Tm) as shown by the arrows (FIG. 1C) and the ability to detect more than one type of target attached to the individual probe spot. The melting curve for the Beta Actin probe spot (FIG. 1C) depicts two distinct melting curves indicating that at least two different types of target DNA were bound.

With this preliminary data in mind, the objectives of the present invention include improving a real-time array reader machine, both instrumentation and software and to demonstrate the ability of the machine to collect melting curve data on microarray slides containing 1000 probe spots or more. In addition, the accuracy or resolution of melting curve analysis was to be sufficient to distinguish between the melting of perfect matched dsDNA and dsDNA with the smallest possible change in sequence, a one base pair mismatch.

The description above and below and the drawings of the present document focus on one or more currently preferred embodiments of the present invention and also describe some exemplary optional features and/or alternative embodiments. The description and drawings are for the purpose of illustration and not limitation. Those of ordinary skill in the art would recognize variations, modifications, and alternatives. Such variations, modifications, and alternatives are also within the scope of the present invention. Section titles are terse and are for convenience only.

Experimental

Fabrication of Custom Microarray Chips

The hybridization, washing, and melting cycles of the Real-Time Array, according to an embodiment of the present invention, requires a strong and durable covalent attachment of probe molecules to ensure repeatability between assays. The epoxysilane coated microarray slides Nexterion Slide E (Schott, Louisville, Ky.) was selected as a most durable product to attach the probes. Probe DNA sequences were 25 base pairs in length (bp) and contained a modified amino 5' terminus containing a 6 amino acid linker. All probe sequences were custom synthesized by IDT (Coralville, Iowa). Slides were professionally printed using a Nexterion Slide E protocol at two different facilities. The first batch of 25 slides was fabricated by the W. M. Keck Center for Comparative and Functional Genomics (Urbana, Ill.), hereinafter "Keck Center", using standard pin printing techniques known to those skilled in the art, producing 150 μM diameter probe spots. However, chemical deactivation with ethanolamine of unreacted epoxy groups after printing was not performed and the slides shipped with a reactive surface. A second batch of 100 custom arrays, was fabricated by Microarray Inc. (Huntsville, Ala.). This batch of slides was printed in an identical manner but after printing the unreacted epoxy groups were chemically deactivated with ethanolamine before shipping.

Probe Sequences and Microarray Layout

Microarrays were fabricated with between 6-8 repeating blocks down the array slide with approximately 100 probes spots per block. The general layout is summarized in table 1. The first and last row of each block contained a set of control probe spots. These consisted of a positive control spots affixed with Cy3 dye which ranged in concentration from 5 μM to 20 μM, blank space(s), an E. coli gene as a negative control, and the gene sequence of interest, mouse GAPDH, in antisense orientation. The mouse GAPDH probe spot was repeated in sense orientation between rows 1-10.

TABLE 1

Probe Spot Layout for Custom Arrays

| Row | Col | Gene | Orientation and Sequence |
|---|---|---|---|
| 1 and 10 | 1 | Cy3 Positive Control *E. coli* Ecs2686 Flagellar Biosynthesis Gene | 5'-TCT TAT TCA GCC TGA CTG GTG GGA A-3'-CY-3 SEQ ID NO: 1 |
| | 2 | Blank | Blank |
| | 3 | | |
| | 4 | | |
| | 5 | *E. coli* Ecs2686 Flagellar Biosynthesis Gene | Sense<br>5'-TCT TAT TCA GCC TGA CTG GTG GGA A-3'<br>SEQ ID NO: 1 |
| | 6 | Mouse GAPDH Gene Antisense Control | Antisense<br>5'-TGA CAA TCT TGA GTG AGT TGT CAT A-3'<br>SEQ ID NO: 2 |
| | 7-10 | Mouse GAPDH Gene | Sense<br>5'-TAT GAC AAC TCA CTC AAG ATT GTC A -3'<br>SEQ ID NO: 3 |
| Rows 2-9 | 1-10 | Mouse GAPDH Gene | Sense<br>5'-TAT GAC AAC TCA CTC AAG ATT GTC A -3'<br>SEQ ID NO: 3 |

Target DNA Sequences

Target DNA consisting of 25 mer synthesized oligos (IDT) with Cy3 or Cy5 dye modifications added to the 5' terminus are shown in table 2. A one base pair mismatch or SNP was added to the targeted DNA at position 13 causing a G to A mutation.

TABLE 2

List of Probe Sequences

| Oligo | Orientation and Sequence |
|---|---|
| Mouse GAPDH Gene Antisense Perfect Match | 5'-TGA CAA TCT TGA GTG AGT TGT CAT A-3'<br>SEQ ID NO: 2 |
| Mouse GAPDH Gene Antisense One by Mismatch | 5'-TGA CAA TCT TGA ATG AGT TGT CAT A-3'<br>SEQ ID NO: 4 |

Hybridization of Microarray Chips

Before hybridization was started a pre-hybridization wash of printed microarrays was performed using Nexterion E Pre-Hyb solution (Schott AG) according to the manufacturer's instructions. Briefly, microarray slides were transferred to clean Coplin jars containing solution preheated at 42° C. for approximately 10 minutes. Pre-hybridized slides were then washed with distilled water ($dH_2O$) for 30 seconds and this was repeated up to five times until no foaming appeared in the solution. Slides were then washed in 2-propanol for 2 minutes and quickly air dried before hybridization.

Alternatively, the same procedure was followed but the 2-propanol treatment step was omitted and slides were incubated with a 1 ml solution of polyethyleneimine (PEI; MW 70000 (Sigma-Aldrich, St. Louis, Mo.)) in variable concentrations ranging between 1%-10% in 2.5×SSC buffer for 20 minutes at room temperature. This was followed by three 30 second washes in 2.5×SSC buffer. Slides were not allowed to dry and the hybridization procedure was immediately started.

A 100 µl hybridization mixture was made from 76 µl hybridization buffer with formamide (Array It Hyblt® 2, Arrayit Corp.), 16 µl $dH_2O$, and 8 µl of target DNA at 250 µM concentration. Between 33 µl to 50 µL of hybridization mixture was applied to each slide before placing a cover slip over the sample. Microarrays were place in hybridization chambers (Arrayit, Corp.) and incubated at 45° C. for 16-24 hours with mild agitation via a rotating shaker in a hybridization oven without humidification.

Post Hybridization Processing

Nexterion E Post Hyb wash solutions of low, medium, and high stringency were used (Schott AG). A Coplin dish was filled with low stringency buffer pre-warmed to 45° C., slides were submerged for 5 minutes, allowing the cover slip to become detached within 30 seconds of being submerged. Subsequently the slides were incubated for 5 minutes each in a series of room temperature buffers consisting of 2 successive medium stringency buffers, 2 successive high stringency buffers. Then, slides were rinsed several times in a dish containing $dH_2O$.

Washed slides were carefully and quickly placed (DNA probe spots facing down) into custom cassettes of the present invention (Real-Time Genomics, Honolulu, Hi.) containing 450 µl of 2.5×SSC so as not to allow the slides to dry out. The cassettes were sealed with water tight and heat resistant tape (Grace-Bio Labs, Bend, Oreg.) and completely filled with 2.5×SSC buffer using a micropipette inserted into the in-port of the cassette, being careful to avoid leaving any air space or air bubbles into the cassette.

Real-Time Melting Assay and Data Processing

A modified Axon 4000a microarray scanner according to the present invention, renamed the RTG 1000, operated using custom software that interfaced the existing GenePix software included with the Axon reader. Before starting each experiment, the RTG 1000 plumbing system was flushed with 2.5×SSC buffer, the thermal control chamber was pre warmed to 44° C., and the scanner focused. The general programmed parameters for the experiment called for successive temperature incubations and washes over a range of 40° C. to 70° C. with temperature increase increments of 1°

C., a temperature hold time of 1 minute, and a 2.5×SSC buffer flush of 600 μl. A scan was then made at 532 nm with starting PMT settings ranging between 600-700 and scan files saved to the hard drive of the computer. As the experiment progressed, after each temperature increase there was an automatic PMT increase of 3 units followed by an automatic focus adjustment increment. These cycles were continued until the last temperature was reached for the range of the experiment.

For each 1° C. increment of temperature change during the experiment a scan file was produced. Typical experiments generated over 20 scan files. Each scan was analyzed using the GenePix software according to the manufacturer's instructions. Briefly, for the first scan at a temperature of 40° C., the file was analyzed with the microarray manufacturers GAL file and GenePix software with a fixed surface area of the spot circle. Once the first scan was analyzed, a GPS file was generated by the GenePix software. The GPS file contained the software parameters used for analysis of the first scan. In order to insure consistency of data analysis, the same GPS file was used to analyze all remaining scans from the experiment.

The resulting scan file produced for each 1° C. increment of temperature contained all the statistical data in a GenePix spreadsheet format termed a GPR file. For each GPR file the column containing the Mean F532-B532 (Mean Fluorescence 532-Background 532) was copied and transferred to a Microsoft Excel Spread sheet. This procedure may be computed by hand but data compiling software was written to automate the task. All graphs were generated with the Excel software program.

Processing of Phalanx One Array Whole Human Genome Chips

Human cDNA samples consisting of Cy3 or Cy5 labeled liver cDNA and heart cDNA samples were obtained from Dr. Chad Walton at the University of Hawaii and were prepared using standard methodologies. These samples were hybridized and processed using the Human One Arrays from Phalanx (Palo Alto, Calif.) in accordance with the manufacturer's protocol.

Summary of Results:
Improvements to the RTG 1000

Figure 2A:
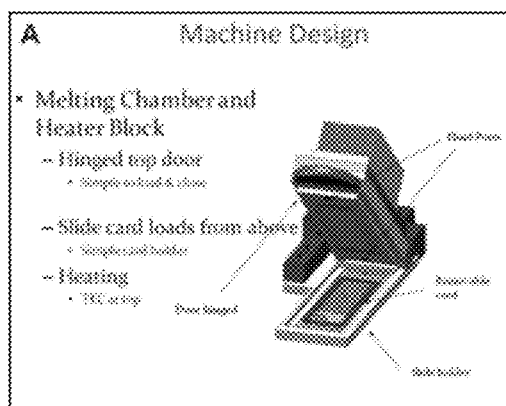
FIG. 2A illustrates the thermal control chamber and heating block of the modified microarray scanner, according to the embodiments of the present invention.
Figure 2B:
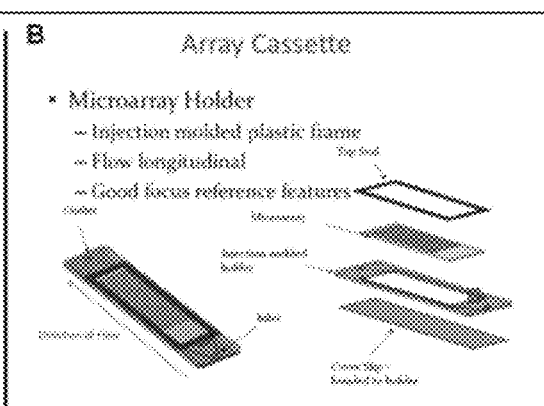
FIG. 2B illustrates the redesigned array cassette of the modified microarray scanner of FIG. 2A according an embodiment of the present invention.
Figure 2C:
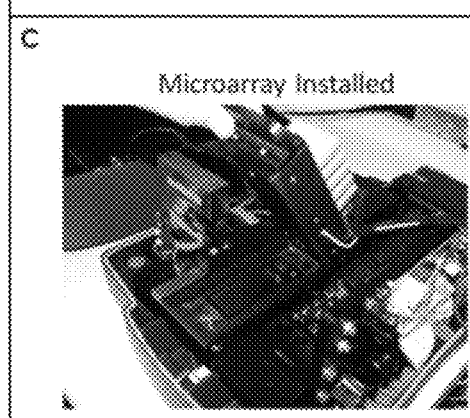
FIG. 2C illustrates the microarray installed in the modified microarray scanner of FIG. 2A according to an embodiment of the present invention.
Figure 2D:
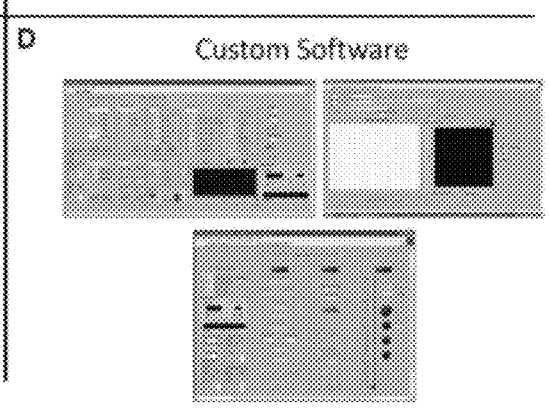
FIG. 2D illustrates screenshots of three custom software programs, according to embodiments of the present invention.

According to an embodiment of the present invention, there is provided an improved microarray reader, RTG 1000, including a redesigned cassette port (FIG. 2A) and cassette (FIG. 2B). The flow and heating characteristics of the device are improved making use and loading of the machine easier. FIG. 2C shows a loaded cassette in place with the objective lens of the reader below the cassette. Three novel software programs were written to operate the machine and help analyze the data (FIG. 2D). Furthermore, computerized Z-axis was added to the thermal control block to speed up the focusing procedure and allow automatic incremental adjustments of focus during experiments (figure not shown).

Analysis of Custom Microarray Chips Produced by the W. M. Keck Center for Comparative and Functional Genomics Aside from control probe spots, the microarray chips produced by the Keck Center at University of Illinois at Urbana-Champaign were, composed entirely of probes to detect the binding of the mouse GAPDH gene sequence. GAPDH is a housekeeping gene that is normally expressed at high levels within mouse cells because of its involvement with glycolysis. Eight blocks or about 800, 150 μM probe spots were replicated on a microarray slide. Duplicate blocks allowed verification of the consistency of results and the large probe spots made scanning detection easier. Arrays were hybridized with excess of target DNA which contained a complementary 25 mer labeled with Cy3 dye.

Figure 3:
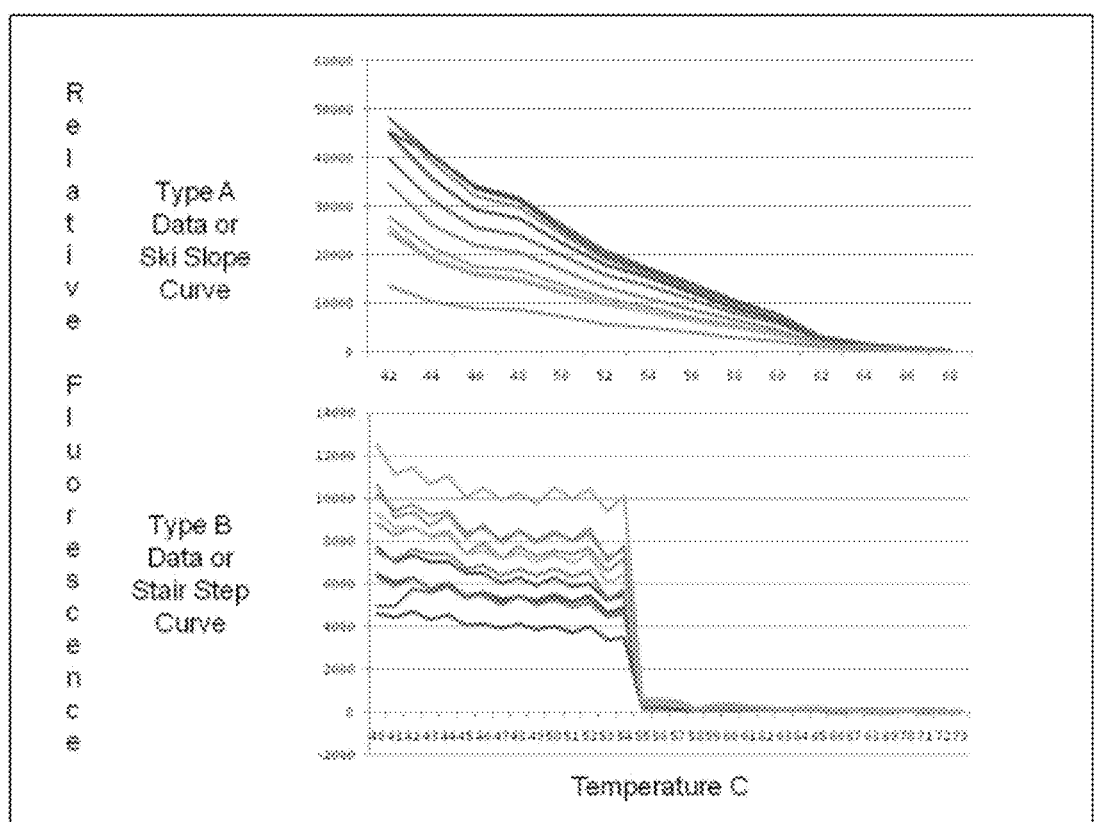
FIG. 3 illustrates a comparison of the initial results obtained with the Keck Center Microarray Chips according to the present invention. A total of 10 probe spots are displayed in each graph. All data is raw and unadjusted.

Unexpected results for the Real-Time Genomics array system of the present invention were achieved after starting experiments with the Keck Center microarray chips. Two very different types of data were obtained with these chips and are shown in FIG. 3. The very first chip analyzed produced a ski slope curve or type A data which represented a gentle downward slope until nearly all of the probe was melted from the chip, in the mid to high 60° C. range. This is unprocessed or raw data without adjustment. A casual inspection of the curve does not reveal a prominent melting point, which would be indicated by a steep downward drop. Rather a shallow downward curve is present ranging from 42° to 68° degrees. As such it is not possible to determine a specific Tm for the bound target DNA. It appears to melt off over a range of greater than 20° C. Note that all 10 probe spots displayed in the graph follow about the same shape of melting curve showing consistency of results. Furthermore, these results were representative of the data obtained from all 8 blocks on the chip. The second chip analyzed in the same experiment under identical conditions produced a stair step or type B curve. The type B data produced a very steep drop-off melting curve. Completely melting off over less than 2.5° C. with a Tm at approximately 55° C. All 10 probe spots in the graph started at different intensities indicating that different concentrations of target bound, but all target melted at exactly the same temperature, showing consistency of results. This data is representative of the 8 blocks on the chip.

As two very different types of curves were generated under identical conditions, experiments were repeated until all chips from the Keck Center were used. As experiments progressed these two distinctly different types of graphs were generated repeatedly with the type A data being about 5 times more common than the type B data. The type B or stair step type data is more preferable since the Tm is easily calculated. Moreover, type B data from the Keck Center chips was also similar to data obtained using commercially made microarray chips (Arrayit Corp., see FIG. 1). Due to some kind of significant procedural difference occurring in the machine, methodology or reagents, further experimentation was conducted.

Accordingly, an improvement to the focus adjustment of the RTG 1000 of the present invention was implemented. The focus was controlled by 3 set-screws that made the stock instrument very difficult to adjust. It is noted that an out of focus machine produced unreadable data and if the RTG 1000 focus began to drift during an experiment the data ended up being distorted. Additionally, as the focus issue was examined, it was found that during an experiment, as the temperature of the buffer 2.5×SSC buffer increased, the refractive index of the buffer also changed causing the focus to go out of adjustment. To correct this problem, a dynamic focus adjusting system was installed which included adding a z-axis to the thermal control block. Once this component was installed the focus was steady as judged by the positive control Cy3 labeled probe spots that remained steady in intensity over the entire experiment (data not shown).

Figure 4:
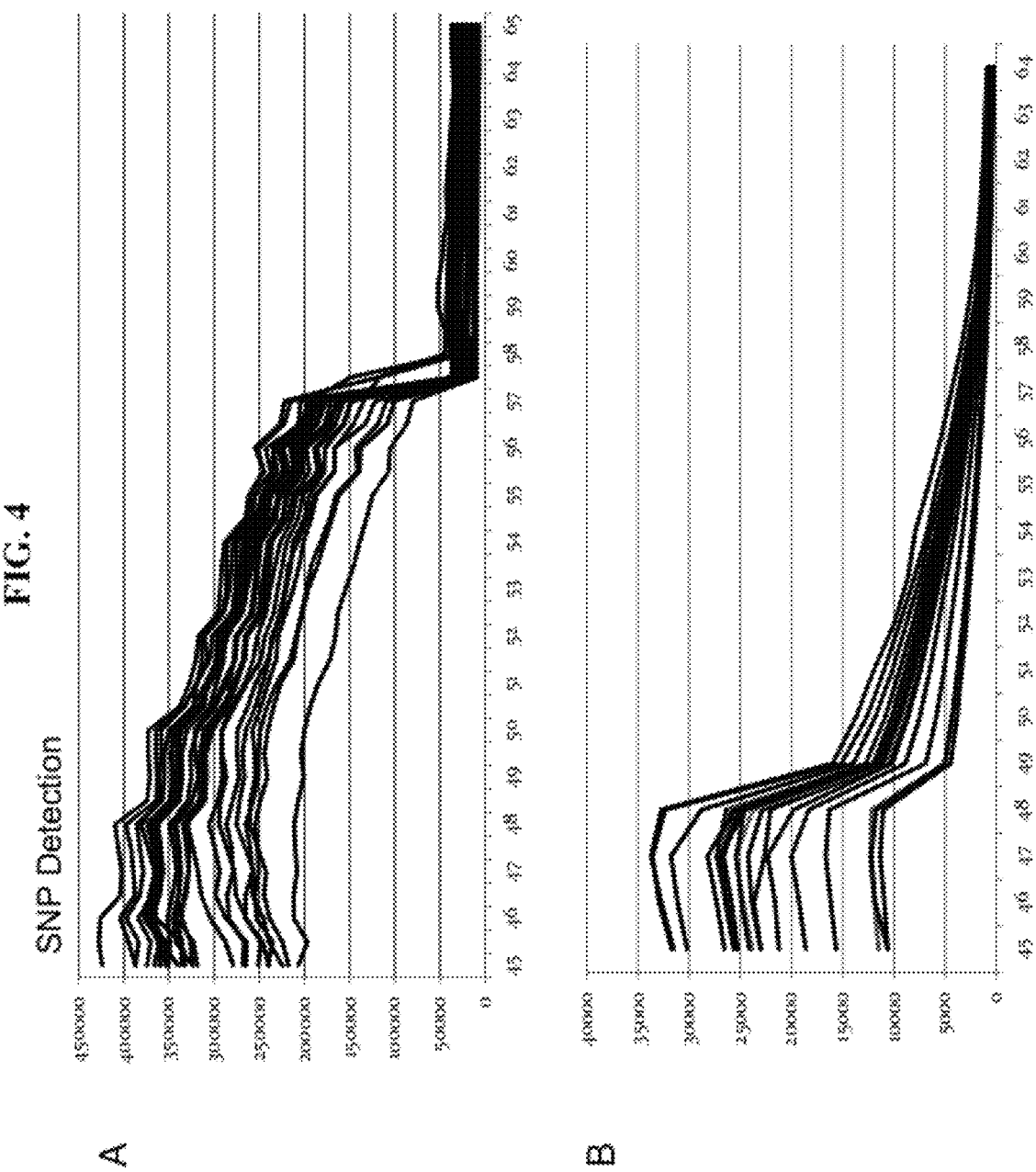
FIG. 4 illustrates a comparison of the melting curves between perfectly matched target and 1 base pair mismatch target binding the 25 mer mouse GAPDH probe sequence according to the present invention. Graph A shows melting curve analysis from a microarray with identical probe spots containing the same 25 mer probe. Note the extremely sharp melting curve and Tm of about 57° C. Graph B is a microarray with the same probe type as graph A but hybridized with target containing a 1 bp mismatch or SNP. Note that the Tm is about 48.5° C. a difference of 8.5° C. compared to graph A.

Further experiment was conducted with remaining Keck Center chips in which the type of target DNA was switched from perfect match to one base pair mismatch or a SNP. All other experimental parameters were the same. Again the type A data was the most common melting curve obtained but some type B data was also observed as shown in FIG. 4. When target DNA containing a one base pair mismatch was used, the measured melting temperature of the target was approximately 48.5° C. or 8.5° C. lower than the perfectly match target (graph A in FIG. 4). The predicted difference in melting temperature using commercially made software for this same reaction under liquid phase conditions was 4.4° C. Therefore, the Real-Time Array of the present invention appeared to both sharpen the melting curve and increase the difference in Tm between perfectly matched and one base pair mismatched targets enhancing detection of SNPs.

Analysis of Custom Microarray Chips Produced by Microarray Inc.

To confirm the results, including the unexplained type A data, or to verify a problem with the Keck Center chips, experiments were conducted on additional chips from another vendor. A set of experiments was conducted with an exact same type of microarray chip was ordered from Microarray Inc. The best of the real-time microarray results showed sharper, easier to read melting curves with increased separation between perfectly matched and one base pair mismatched target, suggesting good SNP detection. Moreover, data obtained from experimentation as shown in FIG. 1C suggested that the technique was capable of discriminating between different types of target bound to the same probe spot. This is evident in FIG. 1C of the beta actin graph in the two distinct Tm's observed, indicating at least two types of target bound. The experiments using the chips from Microarray Inc. were started using a 50:50 mixture of perfectly matched and one base pair mismatched target DNA both labeled with Cy3 dye and hybridized at the same time; the goal of this experiment being to detect the melting of both types target simultaneously on the same probe spot.

Initial experiments using Microarray Inc. chips produced a distinctly different melting curve shape depicted in FIG. 5B. This curve is a classic ski-slope curve with a short plateau at about 43° C. and a downward slope over a range of 44° C. to 64° C. The median Tm might be approximated by the arrow at about 55° C. but the target was composed of two different sequences and should in turn produce two different Tm's. Therefore the Tm for the perfect match and one base pair mismatch was not detected as separate curves but rather blended into one large curve. This result was repeated over several different experiments and is representative data of the 6 blocks printed on the chips. The repeatability of the Microarray Inc. chips was excellent but the sharp steep drop off melting curves that were obtained on the Keck Center chips was not observed.

All results obtained using the Keck Center chips and Microarray Inc. chips were re-evaluated. A key difference in the array fabrication procedure of the sets of chips was then identified. Microarray Inc. performed chemical deactivation of un-reacted epoxy groups with ethanolamine after printing was completed but before shipping to the end user. The Keck Center omitted the deactivation step and shipped the slides with an active surface allowing the end user to perform deactivation if desired. The manufacture of the slides Nexterion Slide E (Schott AG) recommended deactivation with ethanolamine. This prevented unwanted reactions with target DNA other than hydrogen bonds or background substances with the surface epoxide, which may include ozone or airborne hydrocarbons that would produce abnormal signal and distort the results.

This information allowed for interpretation of the results from both the Keck Center and Microarray Inc. slides. The Keck Center slides may have bound target via bonds other than hydrogen bonds or had the capacity to react with abundant levels of ozone and hydrocarbons present in the tropical air of developed areas of Hawaii and certainly present in the room air of the laboratory. The type A curve may possibly be related to the reaction of the chip surface with unwanted agents in the air causing background and unreadable results. Also, it may be possible that the type B results were attained if the chips were processed very quickly and placed in liquid buffer without allowing the room to air to react with the surface.

However, the surface chemistry of the Keck Center and Microarray chips was distinctly different. The active surface of the Keck Center chips contained an epoxide exposed to the surface. The epoxide was intended to react with the amino terminus of the modified probed DNA via a nucleophilic addition where the epoxide functions as an electrophile and the probe molecule as a nucleophile. Since the epoxide is un-reacted, the surface is coated with a strong electrophile, which generally can have a positive chemical charge. The deactivation of epoxide with ethanolamine via a nucleophilic addition changes the surface composition of the slide from epoxide to that of a hydrocarbon with attached hydroxyl group.

Figure 5:
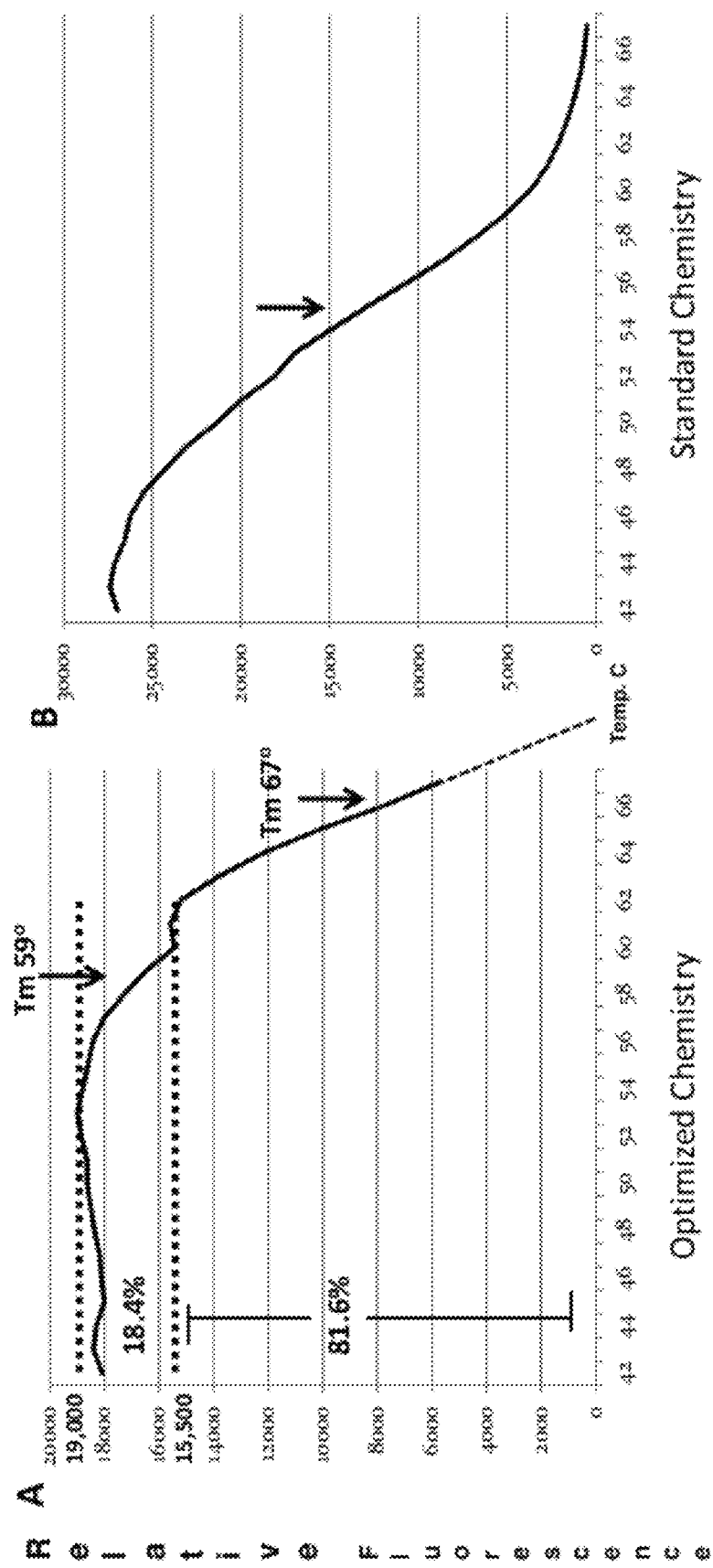
FIG. 5 illustrates an exemplary comparison of the type of melting curves obtained using standard and optimized surface chemistry of Microarray Inc. arrays according to the present invention. Graph A is a melting curve on an array with optimized surface chemistry which is able to detect that approximately 18% of the target bound on this spot is one base pair mismatch (Tm 59° C.) and about 82% perfect match (Tm 67° C.). Graph B is a melting curve on an array with standard surface chemistry and is unable to detect two distinct types of target and instead shows one large melting curve with a Tm of about 55° C. Note that the slope of graph A is steeper and that melting is occurring at a higher temperature.

As shown in FIG. 5, a comparison of the different melting curves obtained between the type B curves (FIGS. 3 and 4) from the Keck Center chips and the Microarray Inc chips (FIG. 5, graph B) suggest that the different chemical characteristics of the active and deactivated chip surface were causing different shaped melting curves. It is possible that the positively charged surface of the active epoxide was in some way reacting with the hydrogen bonds of the bound target DNA and that under specific conditions of increasing temperature and flow, could cause the dsDNA to melt apart with a much sharper curve. This then increased the difference in Tm between perfect match and one base pair mismatch and would help to identify a mixture of target bound to single probe during melting analysis.

Testing was conducted using a proprietary chemical treatment for changing the surface charge of a biosensor. This proprietary mixture comprises of off the shelf chemicals with the primary ingredient being the positively charged polymer polyethyleneimine. Solutions of polyethyleneimine ranging in concentration from 1% to 10% in 2.5×SSC buffer were used to coat the deactivated surface of Microarray Inc. slides before the hybridization mixture was added.

Treatment of Microarray Inc slides with a 1% solution of positively charged polyethyleneimine changed the shape of the melting curve and made detection of the binding of a 50:50 mixture of perfect match and one base pair mismatched target possible (FIG. 5, graph A). During this experiment all other conditions were identical with previous microarrays except for the coating of slides with polyethyleneimine. As depicted in FIG. 5, graph A, this melting curve has two steep drop offs which are presumed to correlate with the melting of one base pair mismatch, Tm of about 59° C., and perfectly matched target with a Tm of 67° C. The difference in Tm between perfectly match and one base pair mismatch was about 8° C. Furthermore, the approximate quantities of dsDNA of each type could be inferred from the amount of relative fluorescence correlated with the melting of each product. This is shown in FIG. 5, graph A and the estimated amounts are 18.4% for one base pair mismatch and 81.6% for perfect match.

Figure 6:
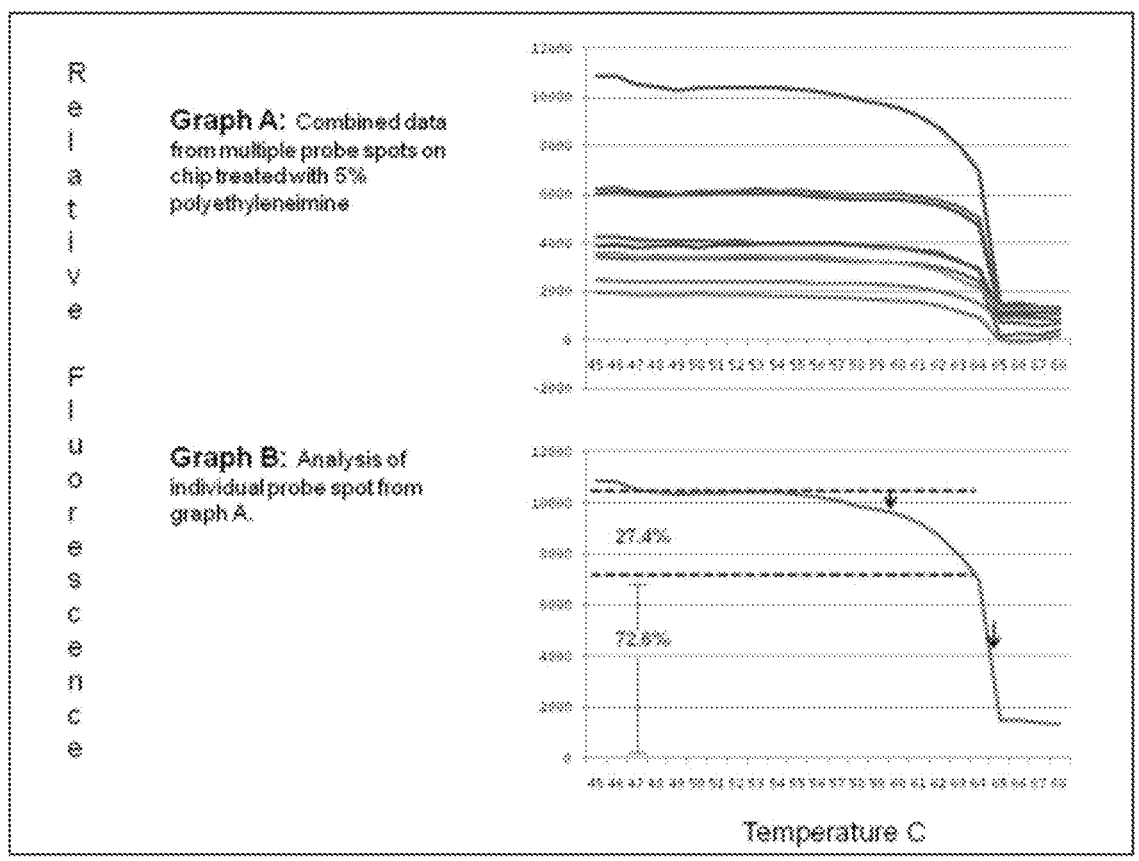
FIG. 6 illustrates exemplary results after treatment of slides with 5% polyethyleneimine according to an embodiment of the present invention.

Since a one percent solution of polyethyleneimine changed the melting curve shape to allow detection of the binding of multiple types of target, pre treatment of slides with a 5% solution was next examined. All conditions were otherwise identical to other experiments and results are shown in FIG. 6. Graph A of FIG. 6 shows the graph of 10 different probe spots and displays a very steep drop off curve with a Tm approximated by an arrow at 64.5° C. All results are raw unadjusted data. Note the consistency of the slope with graphs starting at different intensities, indicating different concentrations of target had bound to these probe spots, but melting away at exactly the same Tm. This graph resembles the shape of type B data from the Keck Center chips shown in FIG. 2 and is distinctly different from Microarray Inc, slides not treated with polyethyleneimine. Therefore, polyethyleneimine treatment appears to have some type of an effect on the binding/melting characteristics of the DNA.

As seen in FIG. 5, the presence of a positively charged surface in close proximity to the nucleic acids melting or dissociating can cause the characteristics of the melting to change. Typically, in classical liquid phase melting or solid phase melting without a positively charged surface, the two complimentary nucleic acids melt apart over a broad temperature range and not a specific temperature point (FIG. 5B). If melting nucleic acids should contain a heterozygous mixture of binding partners of both perfectly matched and one base pair mismatched both present, the melting curves of each species can overlap making the detection of the two species not possible as seen in FIG. 5B. At the beginning of the melting the binding partners containing the one base pair mismatch begin to melt apart. However, before the mismatched partners complete the melting process, the perfect match is already melting apart, generating a melting curve with a smooth ski slope masking the presence of two species of nucleic acid binding partners.

However, in the presence of a positively charged surface, the kinetics of melting can change with a sharpening of the curve. This appears to change the behavior of melting from a process that happens over a temperature range to one that happens over a short temperature transition. The end result is the ability to now distinguish the presence of both mismatch and perfectly match species in melting mixture (FIG. 5A). The melting of the mismatched species is now of shorter and sharper nature and can appear to be completed before the perfect match starts to melt. Typically, this allows the detection and quantification of both species.

According to those of ordinary skill in the art, the reason for the change of melting behavior in the presence of a positively charged surface may not be well known. However, according to one preferred embodiment of the present invention, the presence of a positively charged surface can add an additional force to the melting nucleic acids. Under most conditions, hydrogen bounding is holding the double stranded nucleic acids tighter. Typically, the hydrogen bonding is the force that must be over come during dissociation. In the case of solid phase melting, the presence of a positively charged surface now becomes an additional force together with the hydrogen bonding that may play a role in affecting how the nucleic acids melt apart and sharpening the melting curve. One possible explanation might be that the positive charge helps to hold the labeled strand of nucleic acid more strongly than with the hydrogen bonding alone in a specific spot of the microarray. This holding effect now alters the perceived melting behavior keeping the labeled strand in place longer then letting it melt apart in a very short temperature transition, which is still specific for the sequence of the strand.

FIG. 5, graph A produced a stair step type curve with easy identification of the Tm's for both mismatched and perfectly matched data. However, the identification of two Tm's in FIG. 6 is not easy. Type B data shown in FIG. 3 has only one very steep melting curve which confirms that only one type of perfectly matched target was present. However, FIG. 6 displays two slopes, following from left to right, the slope begins with a shallow convex shape which then turns into an almost vertical line straight down. FIG. 6, graph B breaks the melting curve into sections based on the slope of the curve. If the shallow slope represented the one base pair mismatched target melting away and the steep slope the perfect match melting, then relative amounts of each product could be calculated based on the percentage of fluorescence associated with each slope of the graph. An estimate of each product would be 27.4% one base pair mismatch with a Tm of 59.5° C. and 72.6% perfect match with a Tm of 64.5° C. Further experimentation may be conducted to confirm these estimates. It should also be noted that most but not all of target DNA melted away from the probe spots during the experiment.

Figure 7:
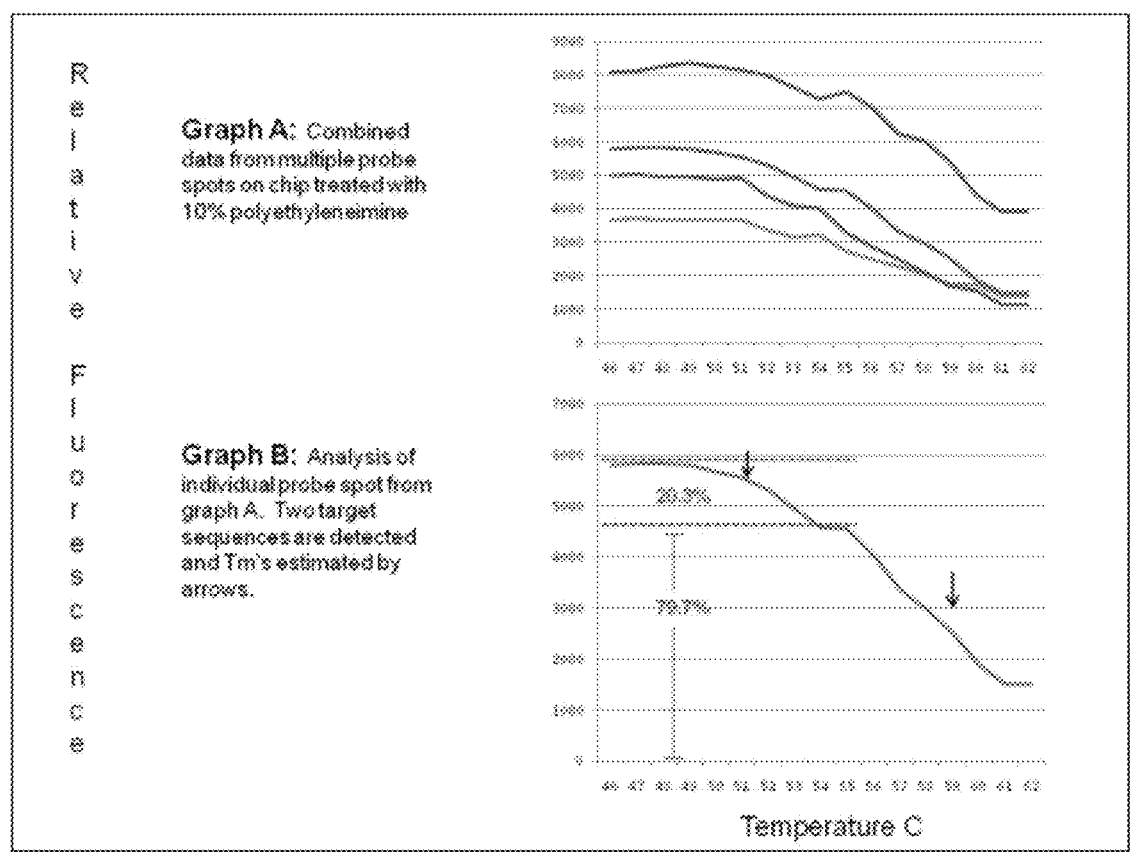
FIG. 7 illustrates exemplary results after treatment of slides with 10% polyethyleneimine according to an embodiment of the present invention.

In the next experiment a 10% solution of polyethyleneimine was used to pre-treat Microarray Inc. slides before hybridization. FIG. 7, graph A depicts a graph of a combination of several probe spots and shows a stair step type curve but with a much shallower slope than shown in FIG. 3 type B data or FIG. 6. The shape of this graph was consistent as multiple probe spots had similar but not exactly the same shape (FIG. 7, graph A). Two distinct Tm's can be observed in the slope of the graph at 51° C. and 59° C. which resembles the shape of curves found in FIG. 5, graph A. The approximate amounts of each target (FIG. 7, graph B) are 20.3% of one base pair mismatch and 79.2% perfect match. These melting temperatures are significantly lower than calculated in FIG. 5A of 59° C. and 67° C. but the difference between Tm's is identical at 8° C. These results further confirm that polyethyleneimine has an effect on the melting of target DNA that helps to distinguish the melting of multiple types of target DNA from the same probe spot. Again it should be noted that most but not all target DNA melted from the probes as the temperature increased.

Analysis of Phalanx One Array Whole Human Genome Chips

Typically, whole human genome chips contained over 30,000 probe spots and probes sequences of 60 base pairs in length. Since the number of probe spots was much higher, the individual spots were much smaller in diameter at 80 µM. One chip was processed with a mixture of Cy3 labeled human liver and Cy5 labeled heart cDNA. This was the first experiment with a large number probe spots and the first two color gene expression profiling microarray experiment. An objective was for the RTG 1000 to be able to read this chip and that the melting curve data would reduce the noise in the measurement. For example, if a given gene was expressed at a 2:1 ratio between two different samples, noise might alter the measured ratio to 1:1. It was hoped that the melting procedure would remove non-specifically bound cDNA at lower melting temperatures. This would result in an improvement in the accuracy of the expression ratio at medium and high temperatures. As the experiment continues, the temperature would become high enough to melt all cDNA from the chip marking the end of the experiment. The final gene expression ratios obtained just before the melting of all cDNA were predicted to be the most accurate. Unfortunately the first attempt failed as the signal from each scan was so weak that the analysis software could not analyze the image file (data not shown). Visual inspection of the picture file confirmed a very weak fluorescent signal across the chip. The cause of this failure was most likely poor dye incorporation during the synthesis of cDNA and more experiments are needed to make this confirmation.

According to an embodiment of the present invention, a working instrument has been provided and method demonstrated for using thermal melting analysis in a microarray format as a novel low cost genomics analysis tool. This technique both improves the accuracy of microarrays and fills gaps not covered well by NGS. Microarray chips manufactured by the W. M. Keck Center for Comparative and Functional Genomics produced some of the most amazing melting curves but not in a consistent manner (FIGS. 3 and 4). To understand the results, an improved microarray reader RTG 1000 has been developed. The improved microarray reader according to an embodiment of the present invention comprises improvements to the machine and its operating system, including the addition of an automatic focusing system which greatly enhanced the consistency and quality of data acquired.

In yet a most preferred embodiment of the present invention, is the effect that the microarray surface chemistry of the microarray has on the actual melting analysis. As discussed, experiments conducted using the Keck Center chips revealed unexpected results, which were determined to be affected by a non standard active epoxide surface coating on these chips. Preferably in the present invention, conventional off the shelf microarrays and supplies are not suitable for Real-Time microarray analysis. This is confirmed by the very consistent melting curve data produced by the Microarray Inc. chips which were ethanolamine deactivated but unable to distinguish between different types of bound target (FIG. 5, graph B).

Typically, DNA melting analysis experiments were performed in tubes or liquid phase with the DNA free in solution. A common limitation to liquid phase melting curves is the inability to achieve one base pair resolution of detection. This methodology normally produces elongated shallow sloped melting curves which are similar to the graphs shown in FIG. 5, graph B. According to the present invention, improving the accuracy of microarrays is affected by a novel and overlooked property of the denaturation of DNA by the combined effects of heat and chemicals. The use of solid phase melting reactions can change the dynamics of the melting curve by creating a nano environment by which both heat and chemistry influence denaturation. In this format, the relevant variables that control the melting reaction can be broken down to heat, solvent flow, and surface chemistry charge. Since the target DNA is bound to the probe DNA, which is in turn bound to the solid surface of the glass array, the chemical composition of the surface of the array influences the denaturation of the DNA.

Figure 8:
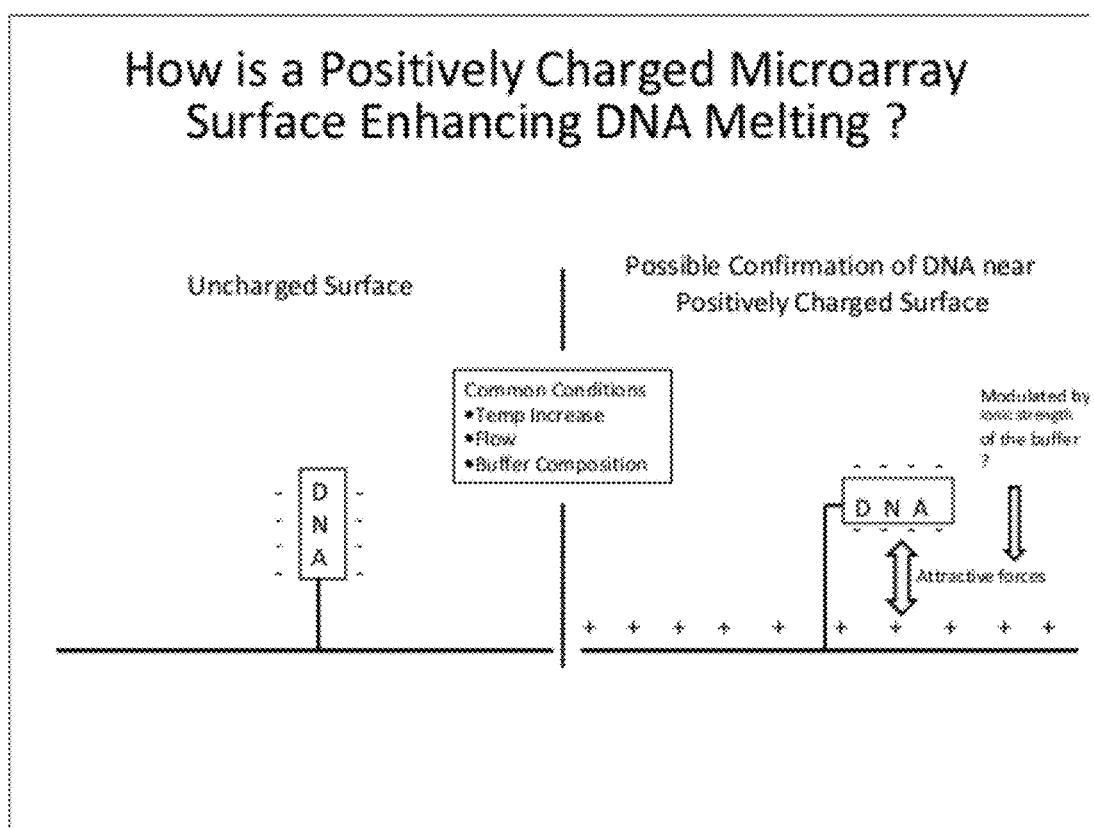
FIG. 8 illustrates an exemplary diagram of how positively charged microarray surface can attract negatively charged nucleic acids directly above the charged surface, enhancing nucleic acid melting according to an embodiment of the present invention.

As seen in FIG. 8, how the surface of the microarray affects the melting of DNA might involve effects on hydrogen bonding between base pairs or the localization of the melted target DNA. The positively charged electrophile (epoxide) present on the Keck Center chips, resulted in a search for a convenient method to apply positive charged surface coatings to the Microarray Inc. slides already in use. Preferably, according to an embodiment of the present invention, polyethyleneimine was chosen to coat the slides. Researchers at University of Hawaii were using this as a cationic agent for surface coating to bind cells on a biosensor. In addition, polyethyleneimine is frequently used as a cationic lipid for the formation of liposomes used in transfection of mammalian cells. It has been determined that the cationic properties of polyethyleneimine cause dsDNA with a net negative charge to condense within the liposome as well as causing some limited denaturation of the double stranded helix.

Supported by the results of the discussed experiments, the present invention provides for the novel use of polyethyleneimine for enhancement of DNA microarray melting curve analysis. Since polyethyleneimine is a solid with a melting temperature of approximately 75° C., it is reasonably believed that the polymer stays on the surface of the glass slide at temperatures below 75° C. allowing interaction with the dsDNA located immediately above the microarray surface. The precise mechanics of this interaction are unknown but the polymers association with denaturation when used in liposomes, suggest conditions on the microarray are promoting denaturation in a manner that allows one base pair resolution of detection. This in turn may imply an effect on the strength of hydrogen bonds between base pairs. It should be noted that the Tm of the perfectly matched targeted DNA decreased as the concentration of polyethyleneimine increased from 1% to 10% suggesting a weakening of hydrogen bonds between base pairs (FIGS. 5, 6, and 7). Another possibility is that the positively charged surface is having an effect on the localization of the melted targeted DNA either causing it to be repelled or attracted to the surface as seen in FIG. 8. A repelling effect might push the target DNA away from the surface and would give the appearance of faster melting or a lower melting temperature. However, DNA generally carries a net negative charge and would likely be attracted to the positive charge of polyethyleneimine (FIG. 8). Experiments with microarrays coated with 5% and 10% solution of polyethyleneimine showed incomplete melting of target DNA (FIGS. 6 and 7) suggesting that the target might be binding the surface of the microarray via other non hydrogen bonding mechanisms. Overall, the observed changes in DNA melting characteristics may be complex and involve more than one type of chemical interaction.

Positively Charged Surface/Effect of Ionic Strength of Buffer

As show in FIG. 8, positive charge on the solid surface typically can attract the negatively charged nucleic acids directly above the charged surface. The exact confirmation of the nucleic acids has not been determined but it is reasonable to assume that the attractive force would cause the negatively charged nucleic acids to bend over into a position which allows it to be in close proximity to the positively charged surface providing the nucleic acids and the method of attachment to the surface is flexible (FIG. 8).

The attractive force between the nucleic acids and the positively charged surface is likely modulated by the composition of the buffer solution. A buffer containing a high ionic strength typically would contain many positively and negatively charged ions that would be attracted towards the positively charged surface and the nucleic acids therefore reducing the perceived attractive forces between the surface and nucleic acids Like wise, a buffer with a low ionic strength typically would have fewer ions to be attracted to the surface and nucleic acids and therefore less effect on the attractive forces between the surface and nucleic acids. This effect could be utilized to modulate the attractive force between the surface and nucleic acids by either reducing or strengthen the attractive force by changing the ionic strength of the buffer (FIG. 8).

The ability to detect the melting of different sequences of target DNA with one base pair sensitivity for each probe spot of a microarray represents a powerful genomic analysis tool with the ability to perform a type of DNA sequence determination or low resolution sequencing at the same cost as a microarray. When used in this format, it functions as more than just a microarray, as it allows for the quick and efficient scanning of the entire genome for the few very important genetic differences that exist between samples. Afterwards, if a more detailed analysis is needed NGS would be performed on the same DNA sample that was hybridized and then selected when melted off the microarray chip. This application would be ideal for rapid screening of a population for genetic differences at a much lower cost than sequencing the entire genome. For example, single nucleotide polymorphisms are always detected by sequencing DNA first before rapid low cost screening tests are developed to detect known SNPs. So SNP detection is limited to the population already sequenced. Screening with a Real-Time array would reduce costs so low the entire population could be screened and in theory detect all SNPs in the population. Another application might be tracking the progress of an infectious disease outbreak or biological weapons attack. In this scenario, a large number of infected patients might be screened to allow characterization of virulence factors, drug resistance, or just obtain epidemiologic information about how the outbreaks progress. NGS is a shot gun approach providing global information from which specific information can be gleaned and is not practically cheap enough to sequence entire populations. Real-Time array screening in turn can focus in on only producing the relevant genomic information needed, saving time, energy and cost.

The present invention provides for technology related to surface chemistry of the array that produces enhanced melting curves. Additional research involves identifying improvements in the chemical coating of the microarray slide with the aim of yielding more durable, sensitive, and consistent results. Additionally, the stringency of the hybridization/melting process needs to be documented. The eluted target DNA from each microarray should be sequenced via NGS to confirm exactly what bound the probe DNA and exactly what is being melted away at given temperatures. Confirmatory testing would facilitate developing specific applications.

Accordingly, the developed method of the present invention serves to identify one base pair differences between different types of target DNA bound to a single probe spot. This has been accomplished on microarray slides containing 600-800 probe spots. An initial attempt to perform this analysis on commercial microarray chips containing over 30,000 probe spots was made but failed for reasons likely related to labeling of the target DNA and not the actual melting analysis. During initial development simplicity of array target density and composition was chosen to avoid any difficulty with interpretation of results. As such, custom microarray slides with 1000 or more probe spots were not ordered. However, it is likely that this technique will work on slides containing a minimum of 1000 probe spots provided the spots were large enough in diameter (>150 µM). It is expected that further development in ability to control the surface chemistry of the slides will help in other applications of the method, such as the characterization of tuberculosis isolates.

According to the present invention, RTG's technology bridges the gap between microarray and Next Generation Sequencing (NSG) and can achieve the accuracy of NGS systems at microarray prices. RTG's technology competes with microarrays but can work with or compete against NGS depending on the application. Preferably, RTG's technology can be used as a capture/enrichment platform, and can more specifically and efficiently capture target DNA than conventional microarray capture systems. More preferably, this technology elutes nonspecific and extraneous DNA at low melting temperatures while retaining stably bound desired target DNA. For NGS, this can increase the efficacy of enrichment while reducing NGS sequencing cost by avoiding the sequencing of unwanted DNA. Additionally, because actual sequencing data can also be obtained by melting curves analysis on the array, the Real-Time Technology can simultaneously capture and re-sequence DNA by association, thereby obviating NGS sequencing.

Throughout the description and drawings, example embodiments are given with reference to specific configurations. It will be appreciated by those of ordinary skill in the art that the present invention can be embodied in other specific forms. Those of ordinary skill in the art would be able to practice such other embodiments without undue experimentation. The scope of the present invention, for the purpose of the present patent document, is not limited merely to the specific example embodiments or alternatives of the foregoing description.

What is claimed is:

1. A method of capture/enrichment, detecting the presence, measuring the amount or verifying the sequence of a target polynucleotide of interest in a test sample without the use of an electric field, comprising the steps of:

(a) forming a reaction mixture by combining in an assay medium:

(i) a first reagent comprising a first probe bound to a positively charged coating on a surface of a solid particle, the first probe comprises a first single stranded nucleic acid fragment complementary to a first of two separated strands of a selected segment of the target nucleotide sequence; wherein the positively charged coating on the surface of the solid particle comprises polyethyleneimine, such that the positively charged coated surface of the solid particle improves stringency during the hybridization by changing the kinetics of unbinding of the target polynucleotide;

(ii) an aliquot of the test sample suspected of containing the target nucleotide sequence, wherein the first probe is complementary to portions of the target polynucleotide sequence;

(iii) an ionic buffer comprising an ion concentration, the ion concentration in the buffer sufficient to provide a shielding effect that modulates hydrogen bond attraction between the target polynucleotide sequence and the probe sequence, and the positively charged coated surface of the solid particle;

(b) subjecting the reaction mixture to denaturing conditions rendering the target polynucleotide sequence in the sample to be single stranded;

(c) incubating the reaction mixture under hybridization conditions to cause hybridization between the first probe and the first strand of the selected segment of the target polynucleotide sequence; wherein the presence of the target polynucleotide, substantially all of the first probe will be hybridized to the first strand of the selected segment of the target polynucleotide sequence to produce a bound target polynucleotide sequence;

(d) washing the reaction mixture;

(e) exposing the reaction mixture to dissociation conditions;

(f) monitoring the reaction mixture by dissociation curve analysis for the dissociation of the target polynucleotide, wherein dissociation of the target polynucleotide correlates with changes in the presence of the bound target polynucleotide and with temperature changes, such that thermal dissociation characteristics are enhanced for analysis as compared to a surface of a solid particle that is not coated with the positively charged coating; and (g) generating a dissociation curve, wherein a one base pair sequence difference between the nucleic acid hybrids in the target polynucleotide sequence and the sequence of the first probe are detected, quantified and differentiated; wherein the temperature range of melting of one base pair mismatched target polynucleotide and a temperature range of melting of perfectly matched target polynucleotide have different temperature ranges of melting and no longer overlap, and wherein the positively charged coated surface of the solid particle changes the kinetics by narrowing the temperature range of melting between the one base pair mismatch and the perfectly matched target polynucleotide to produce a distinctive melting curve with a change in a slope of the curve to form a biphasic melting curve consisting of two separate melting curves, such that the two separate melting curves are separated by a temperature range of about 1° to 17° C. wherein no melting occurs, resulting in a biphasic melting curve of the target polynucleotide of interest in a test sample without the use of an electric field.

2. The method of claim 1, wherein the target polynucleotide is a segment of DNA.

3. The method of claim 1, wherein the target polynucleotide is a segment of RNA.

4. The method of claim 1, wherein the first probe is a DNA or RNA fragment.

5. The method of claim 1, wherein the first probe is bound to the coated surface of the solid particle by a linker.

6. The method of claim 1, wherein the solid particle is a glass or silica.

7. The method of claim 6, wherein the solid particle is a glass slide.

8. The method of claim 1, wherein the polyethyleneimine is present in the amount from about 1% to about 10%.

9. The method of claim 7, wherein the glass slide is a micro array glass slide.

10. The method of claim 9, wherein the micro array glass slide comprises from about 10 to about 4.2 million first probes.

11. The method of claim 1, wherein the target polynucleotide sequence includes a label.

12. The method of claim 11, wherein the label is a fluorescent dye.

13. The method of claim 1, wherein the step of exposing the reaction mixture to melting conditions is carried out over a temperature range from about 0° C. to about 100° C.

14. The method of claim 13, wherein the step of exposing the reaction mixture to melting conditions is carried out with temperature increase increments of from about 0.01° C. to about 5.0° C.

15. The method of claim 1, wherein the steps of forming, subjecting, incubating, exposing, monitoring and generating are carried out by an automated micro array device.

16. The method of claim 1, wherein the first probe includes a label.

17. The method of claim 16, wherein the label is a fluorescent dye.

18. The method of claim 1, wherein the positively charged coated surface is a dipole.

\* \* \* \* \*

SEQUENCE LISTING

<160> NUMBER OF SEQ ID NOS: 4

<210> SEQ ID NO 1
<211> LENGTH: 25
<212> TYPE: DNA
<213> ORGANISM: Escherichia coli
<220> FEATURE:
<221> NAME/KEY: misc_feature
<223> OTHER INFORMATION: Cy3 Positive Control E. coli Ecs2686 Flagellar
      Biosynthesis Gene

<400> SEQUENCE: 1
tcttattcag cctgactggt gggaa                                          25

<210> SEQ ID NO 2
<211> LENGTH: 24
<212> TYPE: DNA
<213> ORGANISM: Mus
<220> FEATURE:
<221> NAME/KEY: misc_feature
<223> OTHER INFORMATION: Mouse GAPDH Gene Antisense Control

<400> SEQUENCE: 2
tgacaatctt gagtgagttg tcat                                           24

```
<210> SEQ ID NO 3
<211> LENGTH: 25
<212> TYPE: DNA
<213> ORGANISM: Mus
<220> FEATURE:
<221> NAME/KEY: misc_feature
<223> OTHER INFORMATION: Mouse GAPDH Gene

<400> SEQUENCE: 3
tatgacaact cactcaagat tgtca                                25

<210> SEQ ID NO 4
<211> LENGTH: 25
<212> TYPE: DNA
<213> ORGANISM: Mus
<220> FEATURE:
<221> NAME/KEY: misc_feature
<223> OTHER INFORMATION: Mouse GAPDH Gene Antisense One bp Mismatch

<400> SEQUENCE: 4
tgacaatctt gaatgagttg tcata                                25
```